United States Patent [19]

Rosskopf

[11] Patent Number: 4,560,979

[45] Date of Patent: Dec. 24, 1985

[54] METHOD FOR TRIGGERING AN ALARM IN AN INFUSION SYRINGE

[75] Inventor: Gerhard Rosskopf, Fuldabrück-Dörnhagen, Fed. Rep. of Germany

[73] Assignee: Intermedicat GmbH, Emmenbrücke, Switzerland

[21] Appl. No.: 591,558

[22] Filed: Mar. 20, 1984

[30] Foreign Application Priority Data

Apr. 22, 1983 [DE] Fed. Rep. of Germany ....... 3314664

[51] Int. Cl.⁴ .............................................. G08B 21/00
[52] U.S. Cl. .................................. 340/540; 340/618; 340/686; 604/131
[58] Field of Search ............... 340/540, 527, 618, 615, 340/612, 686; 604/131, 154; 364/413

[56] References Cited

U.S. PATENT DOCUMENTS

| 3,105,490 | 10/1963 | Schoenfeld | 340/618 |
| 4,308,866 | 1/1982 | Jelliffe et al. | 364/413 |
| 4,437,162 | 3/1984 | Kato | 340/618 |

*Primary Examiner*—Glen R. Swann, III
*Attorney, Agent, or Firm*—Kenyon & Kenyon

[57] ABSTRACT

An infusion syringe pump for forcing an infusion liquid out of the syringe comprises a sensor which is actuated at a certain displacement of a movable piston in the syringe. The residual infusion time before the syringe is completely empty is calculated from the residual volume of liquid left in the infusion syringe upon activation of the sensor, and from the infusion rate. At a given time before expiration of the residual infusion time, an alarm is produced by an alarm device. The alarm is thus always given independently of the particular infusion rate of the syringe and at a predetermined time (e.g. three minutes) before the end of infusion.

2 Claims, 2 Drawing Figures

METHOD FOR TRIGGERING AN ALARM IN AN INFUSION SYRINGE

BACKGROUND OF THE INVENTION

The present invention relates to a method for triggering an alarm in an infusion syringe before the syringe is emptied of infusion liquid.

The use of a syringe pump which continuously forces a liquid such as a drug out of an infusion syringe for injection into the body of a patient is known. Such syringe pumps comprise a holder to which a syringe cylinder is attached and a slide movable relative to the holder, the slide being connected to a syringe piston movable in the syringe cylinder. The slide is moved continuously by a motor drive, so that advance of the syringe piston by the slide forces the injection liquid out of the syringe.

In order to indicate to an attending physician or nurse that the syringe is almost empty, an alarm is produced before the infusion syringe is emptied of infusion liquid. Producing an alarm before the syringe is completely emptied enables the appropriate preparatory measures to be taken, for example, those necessary to replace the near-empty syringe with a new full syringe. In providing such an alarm, known syringe pumps utilize a sensor responsive to a predetermined position of the slide which corresponds to a predetermined position of the syringe piston before its end position.

However, infusion pumps are used not only in connection with a specific syringe size or type, but also with different size and type syringes. Also the rate of advance of the syringe pump slide is adjustable in some syringe pumps so as to be able to attain different rates of infusion, which for example can be in the range of from 0.1 to 99.9 ml/h. With such a wide range of infusion rates, the time which elapses between the activation of the sensor and complete evacuation of the syringe can vary greatly. Normally the sensor is positioned so that at the maximum infusion rate, three minutes elapse between activation of the sensor and emptying of the syringe. If the infusion rate is lower (slower) than the maximum infusion rate, the alarm will be triggered relatively early, so that it does not effectively indicate the time at which the syringe is almost empty. An alarm which is not in a fixed-time relationship with the event it is to announce is practically useless and can even be misleading.

SUMMARY OF THE INVENTION

It is an object of the present invention to provide a method for indicating emptying of an injection syringe a predetermined time before the syringe is actually emptied independently of the infusion rate and/or independently of the syringe size and/or type.

The above and other objects are achieved by the invention disclosed herein, according to which the time to emptying of an infusion syringe or like device, i.e. the residual infusion time, is calculated upon activation of a sensor from the liquid volume remaining in the infusion syringe, i.e., residual infusion volume, and/or from the rate at which the infusion liquid is being removed from the syringe. Based on either and preferably both calculations, an alarm is given a predetermined period of time before expiration of the residual infusion time.

According to a preferred embodiment of the invention, following activation of the sensor, the residual infusion time remaining before complete evacuation of the infusion syringe is determined from the residual volume of the infusion liquid in the syringe and the infusion rate. A period of time is calculated from the residual infusion time and a predetermined time before expiration of the infusion time. This period of time starting with activation of the sensor is then allowed to elapse before an alarm signal is generated so that the alarm will be produced a predetermined time before expiration of the residual infusion time, i.e. a predetermined time before the end of the infusion.

Thus, generation of the alarm signal is not path-dependent as in the known methods, nor is it exclusively time-dependent, as the infusion rate or the velocity of movement of the slide is taken into consideration. If it is desired to produce the alarm signal three minutes, for example, before the end of infusion, the alarm signal will always be produced three minutes before the end of infusion regardless of the infusion rate. This predetermined time period is sufficient for the hospital personnel to make the necessary preparations before the end of infusion. On the other hand, this predetermined time period is not long enough for attending hospital personnel to leave a patient to which the syringe pump is connected in order to carry out other tasks in the meantime.

The calculation described above can be carried out by discrete circuitry or by a microprocessor. Thus, the period of time from the activation of the sensor to alarm triggering can be calculated, for example, by counting a clock signal either in a discrete counting circuit or under control of a microprocessor. However, it is preferred that a microprocessor be used to calculate the remaining infusion time, although this calculation can be effected with an appropriately-designed computing circuit.

The above and other objects, features, aspects and advantages of the present invention will be more readily perceived from the following description of the preferred embodiments thereof when considered with the accompanying drawings and appended claims.

BRIEF DESCRIPTION OF THE DRAWINGS

The present invention is illustrated by way of example and not limitation in the figures of the accompanying drawings in which like numerals indicate similar parts and in which.

DESCRIPTION OF THE PREFERRED EMBODIMENTS

Figure 1:
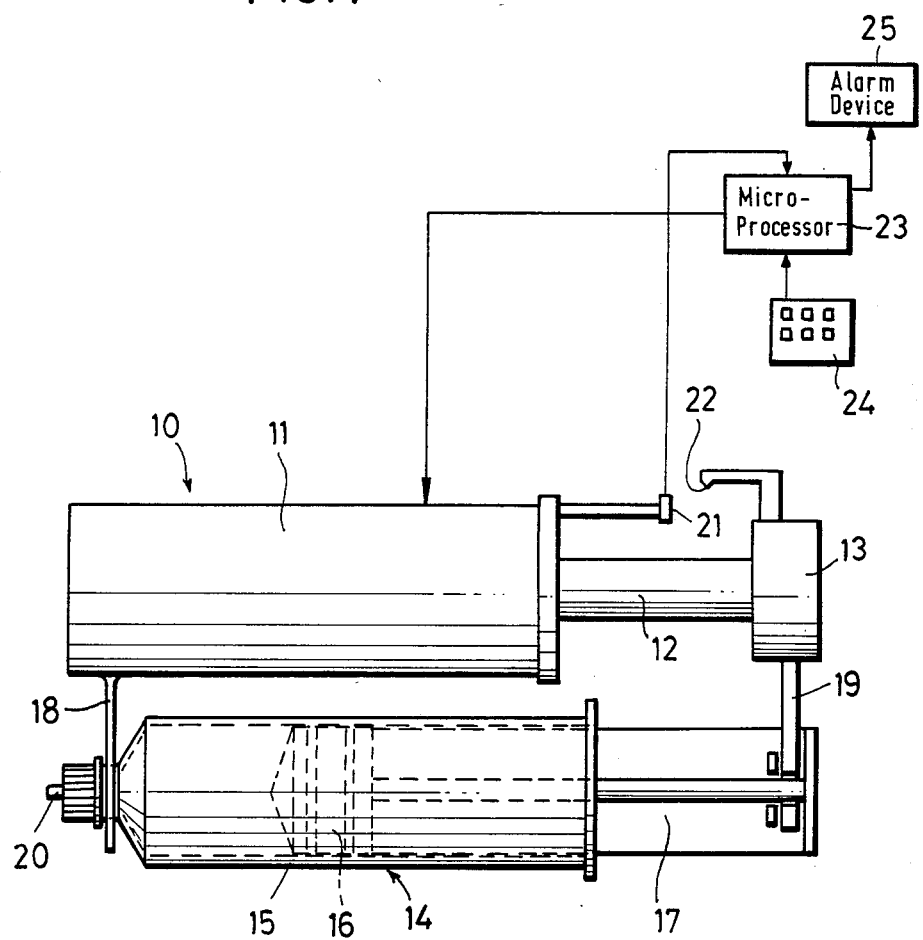
FIG. 1 is a schematic view of an infusion syringe pump used to carry out the method according to the invention.

The infusion pump 10 illustrated in FIG. 1 comprises a housing 11 which contains a drive motor (not shown). The drive motor drives a spindle 12 having an outer end which protrudes from one end of housing 11 and to which a slide 13 is fastened.

The infusion syringe 14 comprises a syringe cylinder 15 and a syringe piston 16 having a piston rod 17. The front end of the syringe cylinder 15 is inserted in a holder 18 which is fastened to the housing 11 of the infusion syringe pump 10. The rear end of the piston rod 17 is inserted into another holder 19, which is connected to the slide 13. When the slide 13 moves in the direction of the housing 11, the syringe piston 16 slides in the cylinder 15 towards its front end and infusion liquid is forced out of the syringe cylinder through the syringe outlet 20. The syringe outlet is in turn connected to the patient by a tube (not shown).

A sensor 21 which is shown schematically in FIG. 1, is fastened to the housing 11 and is activated in a predetermined forward position of slide 13 by an activator 22 fastened to the slide. The sensor 21 may be, for example, a microswitch actuated by a contact cam, or it may be a photocell, a magnetic switch or the like.

The drive of the infusion syringe pump is controlled by a microprocessor 23. Required data, such as syringe volume, infusion rate, etc., is entered into the microprocessor by means of an input keyboard 24. The microprocessor 23 in addition receives the output signal of the sensor 21. The alarm device 25 is also connected to the microprocessor 23 and is activated as described below. The alarm device itself may provide an optical and/or acoustical alarm.

Figure 2:
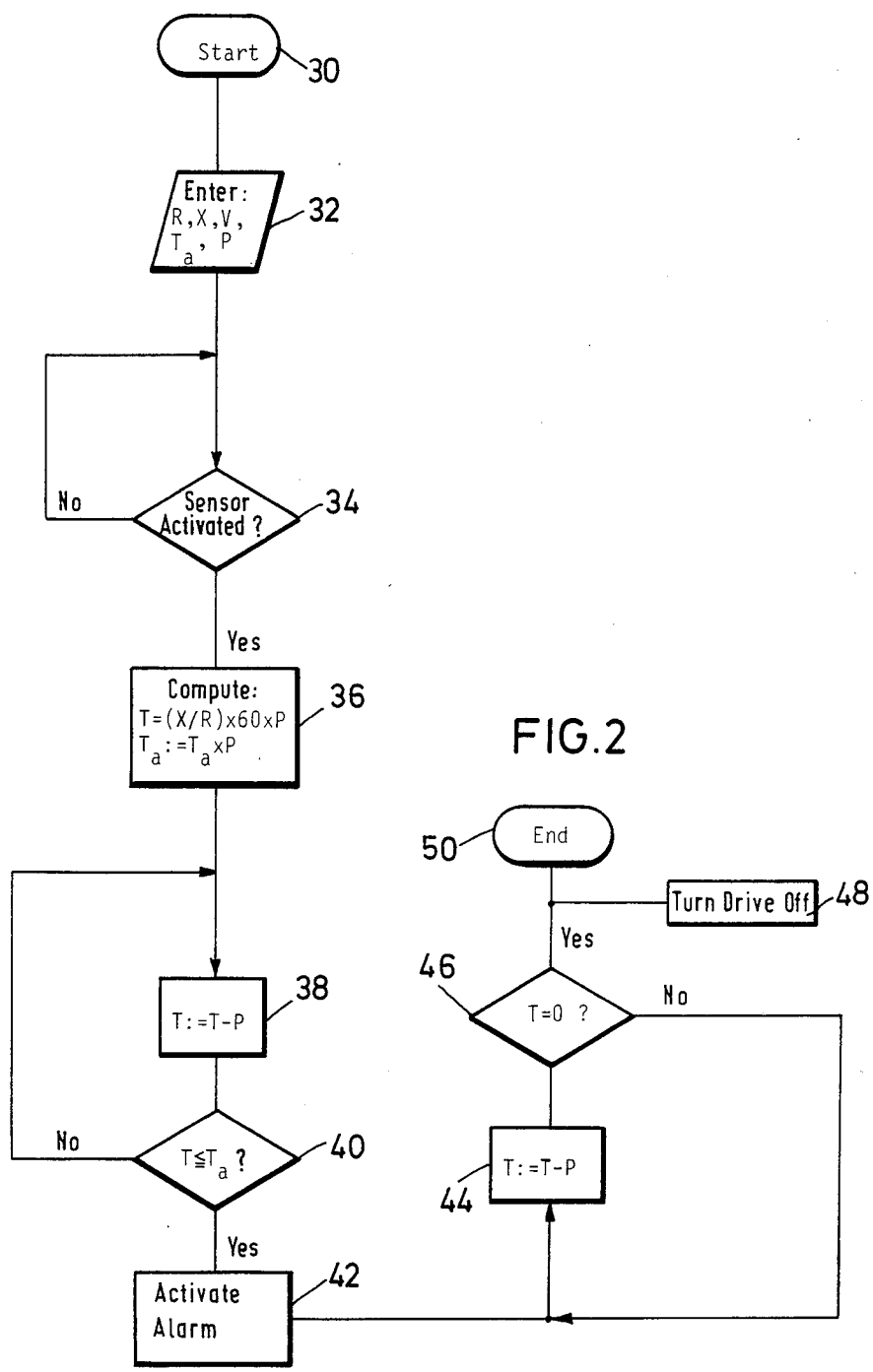
FIG. 2 is a flow diagram of a computer program for carrying out the method of the invention using the apparatus of FIG. 1.

Referring now to FIG. 2, after a start command 30, which is input to the microprocessor at the beginning of the infusion process, the following data is entered into the microprocessor via the keyboard in a data input step 32: the infusion rate R (ml/min), the residual volume X (ml) still in the infusion syringe upon activation of the sensor, the total infusion volume V (ml), the period $T_a$ between generation of the alarm and emptying of the infusion syringe, and the multiplier (cycle factor) P for conversion from minutes to the clock unit of the microprocessor.

After this data has been entered in the microprocessor, a test occurs in step 34 to determine whether the displacement sensor has been activated. If the sensor has not yet been activated, the test is continually repeated until it is. After the displacement sensor has been activated, the remaining infusion time T is calculated in step 36 according to the formula, $$T = (X/R) \cdot 60 \cdot P.$$

in the time units of the algorithm. In addition, the time period $T_a$ from activation of the alarm to the final turn-off of the drive is converted into the clock units of the microprocessor by multiplying by the cycle factor P (per second) in step 36.

In steps 38 and 40 respectively, the residual infusion time is decreased with each clock signal and a test is made to determine whether the residual infusion time T is smaller than or equal to the time $T_a$ for triggering the alarm. If T is greater than the time period between the alarm and syringe emptying, the time count continues unchanged. If however, the residual infusion time has become shorter than the time period between the alarm and syringe emptying, the alarm device 25 is activated in step 42. The time count then continues as per step 44 until the residual infusion time T becomes zero, as determined in step 46. Thereafter, the drive device is turned off in step 48 and the computing operation is terminated in step 50. The infusion syringe is now completely empty.

An advantage of the method described herein, particularly when using a microprocessor, is that not only is triggering of the alarm controlled, but turn-off of the syringe drive as well. A separate cut-off switch which is used in known infusion syringe pumps is therefore not necessary.

Certain changes and modifications of the embodiments of the invention disclosed herein will be readily apparent to those skilled in the art. It is the applicant's intention to cover by his claims all those changes and modifications which could be made to the embodiments of the invention herein chosen for the purpose of disclosure without departing from the spirit and scope of the invention.

What is claimed is:

1. A method for triggering an alarm in an infusion syringe pump of the type having a slide displaced to force infusion liquid out of a syringe and a sensor activated by the slide before reaching its end position, comprising calculating the residual infusion time upon activation of the sensor from the residual volume in the infusion syringe and the infusion rate, and providing an alarm a predetermined time before expiration of the residual infusion time.

2. The method according to claim 1 and including the steps of calculating a period of time from the residual infusion time and the predetermined time before expiration of the infusion time, allowing this period of time to elapse from activation of the sensor, and thereat providing the alarm.

* * * * *